US000001168H

United States Statutory Invention Registration [19]

[11] Reg. Number: H1168

McKenna et al.

[43] Published: Apr. 6, 1993

[54] INHIBITORS OF PROTEIN KINASE C ACTIVITY AS PROTECTORS AGAINST SEPTIC SHOCK AND REDUCERS OF ARDS

[75] Inventors: Thomas M. McKenna, Rockville; Taffy J. Williams, Gaithersburg, both of Md.

[73] Assignee: The United States of America as represented by the Secretary of the Navy, Washington, D.C.

[21] Appl. No.: 748,307

[22] Filed: Aug. 21, 1991

[51] Int. Cl.[5] ..... A01N 43/04; A01N 33/18; A01N 31/00

[52] U.S. Cl. ..... 514/28; 514/727; 514/738; 514/739; 514/921

[58] Field of Search ..... 514/727, 738, 739, 921, 514/28

[56] References Cited

U.S. PATENT DOCUMENTS 4,816,450 3/1989 Bell ..... 514/25
5,010,059 4/1991 Schmidt ..... 514/25

OTHER PUBLICATIONS

Hannun & Bell, Science, vol. 243, pp. 500–506, (Jan. 1989).
Merrill & Stevens, Biochimica & Biophysica Acta, vol. 1010, pp. 131–139 (1989).
Igarashi et al., Biochemistry, vol. 28, pp. 6796–6800, (1989).
Merrill et al., Biochemistry, vol. 28, pp. 3138–3145, (1989).

*Primary Examiner*—Robert L. Stoll
*Assistant Examiner*—Joseph D. Anthony
*Attorney, Agent, or Firm*—William C. Garvert; A. David Spevack

[57] ABSTRACT

An agent and treatment for a subject susceptible to septic shock. The subject is treated with a PKC inhibitor, preferably wit a PKC inhibitor selected from the group consisting of lipid analogues. Preferred among the lipid analogues are sphingosine and its analogues. The inhibitors of this invention are administered, preferably by infusion in a suitable pharmaceutical carrier, in a range of 0.1 to 50 mg/Kg body weight preferably in the range of 0.5 to 25 mg/Kg body weight and most preferably in the range of 1 to 5 mg/Kg body weight.

8 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INHIBITORS OF PROTEIN KINASE C ACTIVITY AS PROTECTORS AGAINST SEPTIC SHOCK AND REDUCERS OF ARDS

BACKGROUND OF THE INVENTION

1. Field of the Invention

This invention relates to agents and therapy to lessen morbidity and mortality by protecting against septic shock and Adult Respiratory Distress Syndrome (ARDS). More specifically, the invention relates to therapy with Protein Kinase C (PKC) inhibitors to protect against septic shock and reduce ARDS.

2. Description of the Prior Art

Septic shock is defined in the medical dictionaries as a type of shock associated with overwhelming infection. Most commonly, the infection is produced by gram-negative bacteria although other bacteria, viruses, fungi and protozoa may also be causes. As summarized in Infectious Diseases and Medical Microbiology, 2nd edition, edited by Braude et al., Chapter 92, pages 700 et seq.

> "Shock is a syndrome of generalized metabolic failure resulting from prolonged inadequacy of tissue perfusion. Its early clinical manifestations reflect malfunction of those organs most dependent on uninterrupted blood flow, particularly the brain, as well as compensatory adjustments designed to maintain adequate arterial pressure. As these adjustments fail, urinary output decreases and biochemical indices of distorted metabolism are detectable; specifically nonoxidative glycolysis with low yield of high energy chemical bonds testifies to the widespread nature of the disorder. In the end, it is the failure of energy production rather than damage to a particular organ that leads to death.
>
> Other terms, such as 'circulatory collapse,' 'circulatory failure,' and 'hypoperfusion,' have been substituted for 'shock' in an attempt to pinpoint the specific nature of the derangement. When it occurs as a specific complication of infection, it is referred to as 'infectious shock,' 'septic shock,' 'bacteremic shock,' and even 'endotoxin shock.' The last three terms specifically implicate bacterial infection and are therefore too restrictive. Because 'infectious shock' is sufficiently broad as well as concise, this term will be used in the present chapter.
>
> Shock may occur in the course of almost any severe infection, but it is particularly characteristic of bacteremia due to gram-negative bacilli. . . . The importance of endotoxin, the lipopolysaccharide (LPS) composing part of all gram-negative cell walls, is readily apparent because it produces a similar syndrome in experimental animals. Partly because of the extensive use of endotoxin as an investigative tool, endotoxin shock is commonly regarded as the prototype of infectious shock."

The shock is believed to be caused by the action of endotoxins, other products of the infectious agent, or host mediators released in response to the infectious agent on the vascular system. Such action causes altered patterns of perfusion of tissues, and large volumes of blood to be sequestered in the capillaries and veins.

Research by others into PKC inhibition and treatment of inflammatory responses have disclosed that endothelial cells express adhesive proteins in response to sepsis associated stimuli such as endotoxin and cytokines such as interleukin-1 (IL-1) and Tumor Necrosis Factor (TNF). Magnuson et al. (1) and Lane et al. (2) have shown that these adhesive proteins can be reduced on endothelial cell surfaces by inhibition of PKC with staurosporine or 1-(5-isoquinolinylsulfonyl)-2-methyl piperazine (H7). Surface presentation of these adhesive proteins enhances white blood cell infiltration and activation which can result in tissue damage in high inflammatory states like septic shock. In addition, PKC activation enhances endothelial cell permeability resulting in edema. This response to inflammatory agents was also abrogated by exposure of the cells to the PKC inhibitor H7 (3).

Both endotoxin and endotoxin induced mediators (e.g. IL-1 and TNF) have significant effects on vascular smooth muscle contractile performance (13,14). These agents reduce blood vessel contractile strength and sensitivity to agonists that regulate blood pressure; therefore contributing to the poor tissue perfusion characteristic of septic shock. The use of PKC inhibitors to protect vascular smooth muscle against endotoxin and mediator effects on contractile function has not been demonstrated.

Merrill et al. (19) identified that the lipid, sphingosine, is capable of inhibiting PKC in vivo and in vitro. Sphingosine analogues have also been reported to have PKC inhibitory activity (42). Hannun et al. (43) discuss the functions of sphingolipids and sphingolipid breakdown products. The sphingolipids' properties as a PKC inhibitor are discussed as well as the possible pharmacological applications of that inhibition potential as tools to study PKC and its functions. Sphingosine has significant effects on cell physiology (19,43) and is metabolizable because it is a natural membrane component of cells. The usefulness of sphingosine and its analogues as therapies in vivo has not been demonstrated especially in relationship to septic shock and vascular regulation.

Investigations into the influence of PKC in vascular smooth muscle function have primarily been concerned with delineating the role of PKC in contraction. Protein kinase C modulates many aspects of receptor and nonreceptor mediated contractile signal transduction and produces diverse effects on vascular cell contractile responsiveness and calcium homeostasis. Activation of PKC with phorbol esters results in enhanced sensitivity of the contractile mechanism to $Ca^{2+}$ and therefore augments contraction in ferret and rat aortas and the rat mesenteric artery (4,5). Activation of PKC by phorbol diesters increases cellular $Ca^{2+}$ influx in rat and rabbit aortas (6,7). In contrast, in cultured rat aortic smooth muscle cells, phorbol esters enhance $Ca^{2+}$ efflux via a plasma membrane $Ca^{2+}$ pump (8), and inhibit influx through voltage-dependent $Ca^{2+}$ channels (9). Phorbol ester treatment of rabbit aortic smooth muscle cells enhances $Ca^{2+}$ efflux, abolishes the $Ca^{2+}$ efflux that normally occurs in response to norepinephrine, and significantly reduces $\alpha_1$-adrenergic receptor number (10). In cultured rat aortic smooth muscle cells, exposure to a phorbol ester increases $Ca^{2+}$ efflux from the cells and inhibits angiotensin II induced breakdown of $PIP_2$ without altering receptor number or affinity (11). Treatment of rat aortic smooth muscle cells with a phorbol ester attenuate $PIP_2$ hydrolysis and $Ca^{2+}$ efflux in response to vasopressin; in this study the phorbol ester also had no effect on receptor number and it is suggested that the diminished responsiveness possibly results from the uncoupling of vasopressin receptors from guanine nucleotide binding protein (12).

Treatment of septic shock is complex, requiring therapies directed at ameliorating the source of infection [antibiotics], blocking effects of products of the infectious agent and inflammatory mediators on tissues [anti-endotoxin (Young et al. U.S. Pat. No. 4,918,163) and anti-cytokine agents [(Mandell et al. U.S. Pat. No. 4,965,271)], and maintenance of cardiovascular function [volume expansion and pressor agents]. However, mortality still runs at about 100,000 patients per year (40 to 50% of those in shock) and no therapies are available to prevent vascular contractile defects.

SUMMARY OF THE INVENTION

Accordingly, an object of this invention is a therapy to lessen morbidity and mortality caused by septic shock.

Another object of this invention is a formulation of a PKC inhibitor to afford protection against septic shock.

An additional object of this invention is a method of treating the symptoms of septic shock.

Yet another object of this invention are agents to prevent vascular contractile defects associated with manifestations of septic shock.

These and additional objects of the invention are accomplished by treating the subject susceptible to septic shock with a PKC inhibitor, preferably with a PKC inhibitor selected from the group consisting of lipid analogues. Preferred among the lipid analogues are sphingosine and its analogues. The inhibitors of this invention are administered, preferably by infusion in a suitable pharmaceutical carrier, in a range of 0.1 to 50 mg/Kg body weight preferably in the range of 0.5 to 25 mg/Kg body weight and most preferably in the range of 1 to 5 mg/Kg body weight.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
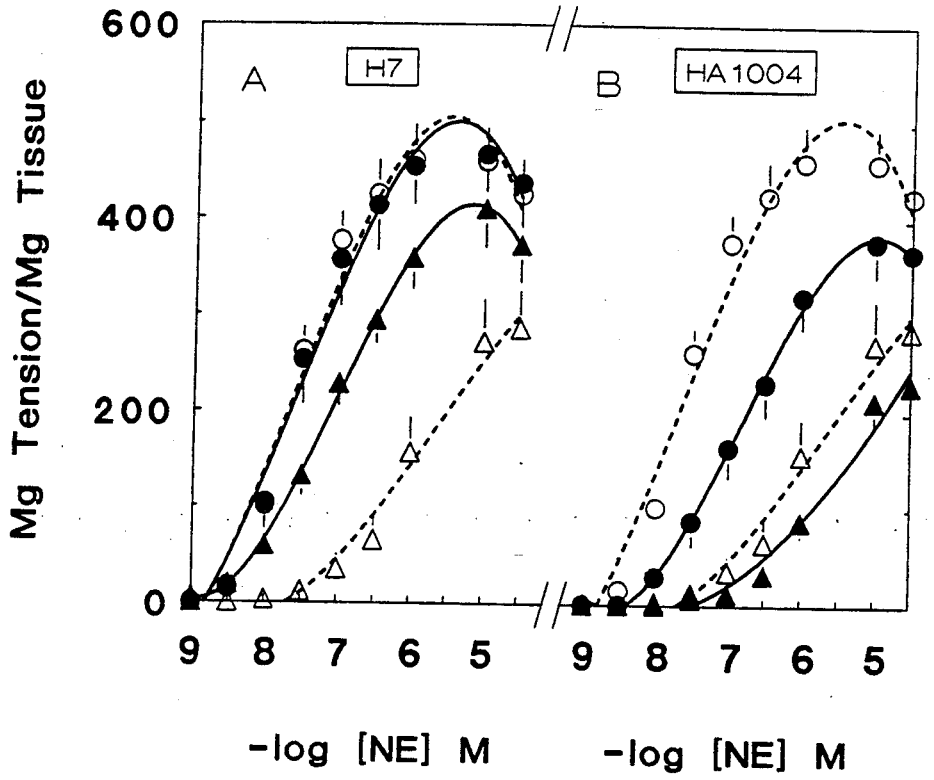
FIG. 1 is a graph showing contraction to cumulative doses of NE by rat aortic rings incubated for 16 hr in combinations of control, LPS (endotoxin or lipopolysaccharide), H7, and N-(2-guanidinoethyl)-5-isoquinolinesulfonamide (HA1004; a negative control for H7) treated media. (Panel A) Responses by rings incubated in medium only (open circles), medium plus H7 (25 μM, closed circles), medium containing LPS (10 ng/ml, open triangles), and medium containing LPS plus H7 (closed triangles). (Panel B) For clarity in presentation, responses by rings incubated in medium only (open circles) and LPS treated medium (open triangles) are reproduced from Panel A. Additional rings were incubated in medium plus HA1004 (25 μM, closed circles), and medium containing LPS plus HA1004 (closed triangles). Six rings were prepared from each rat and one ring allocated into each medium formulation. The responses are plotted as means±SEM; small SEM do not extend beyond the symbols. The curves are the best fit of the data by nonlinear least squares to a polynomial model. N=8 rats.

Rat aortic tissue responds to sepsis and the sepsis-associated mediators IL-1, TNF, and LPS with diminished contractile performance (13,14) and therefore forms a good indication of agents that will provide therapy against septic shock. The present invention shows that vascular contractile suppression induced by long-term exposure of aortic tissue to small amounts of LPS in vitro is mediated by PKC. In specific, it was found that vascular tissue is shielded from LPS-induced vascular suppression by PKC inhibitors. The PKC inhibitors are preferably selected from the group consisting of lipid analogues. Preferred among the lipid analogues are sphingosine and its analogues. The term sphingosine is sometimes used generically to include 4-trans-sphingenine (sphingosine), dihydrosphingosine (sphinganine), 4-D-hydroxysphinganine (phytosphingosine) and homologs and analogues. Representative homologs and analogues, intended to be incorporated herein, are identified in Table 1 of reference (19).

The inhibitors of this invention are administered, preferably by infusion in a suitable pharmaceutical carrier, in a range of 0.1 to 50 mg/Kg body weight preferably in the range of 0.5 to 25 mg/Kg body weight and most preferably in the range of 1 to 5 mg/kg body weight. The inhibitors such as sphingosine and its analogues are not soluble in water. To administer these agents, a solution of sphingosine is made by dissolving the lipid sequentially in ethanol, polyoxyethylene sorbitan mono-oleate (Tween 80), and polyethylene glycol 300 molecular weight (PEG 300) followed by mixing the dissolved lipid with albumin (final aqueous solution contained 10% ethanol, 2.3% Tween 80, 20% PEG 300, and 20% albumin). Alternatively, the sphingosine solution can be prepared by including it as one of the lipids in a lipid mixture and then converting the mixture into a liposome suspension by any of several known techniques.

Having described the invention, the following examples are given to illustrate specific applications of the invention including the best mode now known to perform the invention. These specific examples are not intended to limit the scope of the invention described in this application.

EXAMPLE 1

Tissue preparation and incubation. Male Sprague-Dawley rats (250–350 g, Taconic Farms, Germantown, N.Y.) were used. Rat thoracic aortic rings were prepared and incubated as detailed by McKenna (14). In brief, 4 or 6 rings were prepared from each rat. Care was taken during dissection to maintain the patency of the endothelium. Some aortas were de-endothelialized before sectioning into rings by perfusion with phosphate buffered saline (PBS) containing 1% deoxycholate for 30 sec followed by a PBS and bubble rinse for 5 min. Rings were incubated in DME (Dulbecco's Modified Eagle's medium) supplemented with 1% fetal calf serum, 100 μg/ml streptomycin, and 100 U/ml penicillin. During incubation, the rings were exposed to combinations of LPS (10 or 35 ng/ml), H7 (25 μM), HA1004 (N-(2-guanidinoethyl)-5-isoquinolinesulfonamide) (25 μM), sphingosine (20 μM), or their vehicles. Other rings were incubated with PDB (0.1, 1, and 10 μM) or 4α-PDB (10 μM). Rings used in measures of contractile performance were placed individually in Petri dishes containing 1.2 ml DME and were distributed so that tissue isolated from each aorta was allocated to every combination of treatments within an experiment. Tissue used for measures of PKC content was incubated by placing 3 rings into 2.4 ml of DME supplemented as detailed above that contained LPS (10 ng/ml), PDB (1 μM), or vehicle. All tissue isolated from an aorta (six rings) was allocated to a single treatment. The media and rings were rotated gently for 16–18 hr in an incubator at 37° C. under a 95% $O_2$-5% $CO_2$ atmosphere.

Measurement of aortic ring contraction. After incubation, rings were mounted in tissue baths, equilibrated, and pre-contracted as previously detailed (14). These procedures required approximately 90 min. Rings were maintained in Krebs Ringer Bicarbonate buffer (KRB, 14). Contractions by six or eight rings were measured simultaneously and recorded on multichannel strip chart recorders. Rings were contracted by step wise cumulative additions of norepinephrine (NE, 1 nM to 30 μM), or PDB (10 to 1000 nM). Other rings were contracted by withdrawing KRB from the tissue baths and adding increasing volumes of a high KCl KRB (120 mM, made by equimolar substitution of KCl for NaCl) to the baths to yield final KCl concentrations of 10 to 80 mM. All rings were blotted and weighed after experiments were completed.

EXAMPLE 2

Protein kinase C isolation and assay. PKC was isolated from endothelium-intact and deendothelialized aortic rings exactly as detailed by Thomas et al. (15). After incubation, six rings originally isolated from an individual aorta were homogenized in a Dounce homogenizer. The homogenate was centrifuged and the soluble fraction retained for measures of cytosolic PKC. The pellet was washed, centrifuged, re-homogenized, and a non-ionic surfactant such as Nonidet P-40 added to the particulate suspension to a final concentration of 1% to solubilize any PKC tightly associated with the membrane fraction. Soluble and particulate preparations were subjected to ion-exchange chromatography on DEAE-cellulose, with leupeptin immediately added to all eluted sample fractions. PKC activity in the column eluates was measured on the same day with a commercially available kit. PKC activity was assayed using the manufacturer's protocol and was expressed as $^{32}P$ transferred to a peptide substrate by PKC; phosphorylation of the substrate by calcium and phospholipid independent kinase activity was corrected for by subtracting the radioactivity transferred in a lipid free assay system containing EGTA. The transferred radioactivity was quantitated by scintillation spectrophotometry.

Protein content of the soluble and particulate fractions was measured by bicinchoninic acid assay.

Statistics. Aortic ring contractile performance to NE, KCl, and PDB was characterized by deriving $E_{max}$ (maximum generated tension) and $EC_{50}$ values (concentration of agonist causing a half-maximal contraction) with a nonlinear regression analysis program (16) that fitted second or third-order polynomials to ring dose-responses. Tests for differences between $EC_{50}$ values were based on log $EC_{50}$ values (17). $EC_{50}$ values were then converted to arithmetic means to allow expression as nanomolar concentrations. Examination of differences among four or six treatment means was by randomized blocks analysis of variance; if significant differences were present, then pairs of means were tested by Student-Newman-Keuls a posteriori tests (18). Paired t-tests were used to assess differences between two treatment means. The effect of LPS and PDB treatment on PKC content of vascular tissue was assessed by independent t-tests with Bonferroni correction for multiple comparisons. Differences with probabilities of 0.05 or less were accepted as significant. All data are expressed as means±SEM.

Materials. DME was purchased from Gibco, Grand Island, N.Y. FCS was obtained from Hyclone Laboratories, Logan, Utah. Penicillin/streptomycin and PBS were bought from Quality Biological, Gaithersburg, Md. 4α and PDB was purchased from LC Services, Woburn, Mass. Norepinephrine bitartrate, leupeptin, and D-sphingosine were obtained from Sigma Chemical Co., St. Louis, Mo. H7 and HA1004 were purchased from Calbiochem-Behring Corp., San Diego, Calif. LPS (*E. coli* lipopolysaccharide serotype 055:B5) was purchased from Difco, Detroit, Mich. The LPS was stored as a stock preparation in DME (1 mg/ml). For experiments, the LPS stock was diluted into DME and sonicated for 3 min at maximum power in a cup horn sonicator (Cole-Parmer Instruments, 4710 series, Chicago, Ill.). D-sphingosine was prepared by modification of the technique of Merrill et al. (19). The lipid was solubilized in absolute ethanol to a concentration of 33 mM; this solution was then added in a ratio of 1:100 (v/v) to FCS, incubated at 37° C. for 1 hr, and stored at −20° C. H7 and HA1004 were dissolved in PBS at 1 mg/ml and stored at 4° C. in the dark. Phorbols were diluted in DMSO (dimethyl sulfoxide) (2.5 mg/ml) and stored at −80° C.

EXAMPLE 3

Influence of PKC inhibitors on LPS-induced vascular suppression. Incubation of aortic rings with LPS resulted in significant impairments in sensitivity (Table I) and maximal contraction to NE (FIG. 1).

TABLE I $EC_{50}$ Values for NE and KCl Stimulated Intact and De-Endothelialized Rat Aortic Rings after Incubation for 16 h with Control or LPS-treated Media and PKC Inhibitors.

| | Ne (nM)* | | KCl (mM)* | |
|---|---|---|---|---|
| Treatment | Control | LPS | Control | LPS |
| | Intact Endothelium | | | |
| None | 38 ± 5 | 2020 ± 529§ | 30 ± 1 | 41 ± 4§ |
| H7 (25 μM) | 51 ± 15 | 99 ± 28 | 28 ± 1 | 32 ± 2 |
| HA1004 (25 μM) | 186 ± 43§ | 2757 ± 350§ | 36 ± 3 | 49 ± 4§ |
| N[1] | (8) | | (6) | |
| | De-Endothelialized | | | |
| None | 21 ± 6 | 579 ± 165§ | 25 ± 2 | 34 ± 2§ |
| Sphingosine | 21 ± 8 | 124 ± 54§ | 24 ± 2 | 27 ± 1 |

TABLE I-continued $EC_{50}$ Values for NE and KCl Stimulated Intact and De-Endothelialized Rat Aortic Rings after Incubation for 16 h with Control or LPS-treated Media and PKC Inhibitors.

| | Ne (nM)* | | KCl (mM)* | |
|---|---|---|---|---|
| Treatment | Control | LPS | Control | LPS |
| (20 μM) | | | | |
| N | (7) | | (7) | |

*Log $EC_{50}$ values (concentration of agonist causing a half-maximal contraction) were used to determine whether significant differences were present between treatment groups; the data were then converted to arithmetic means and standard errors to allow the $EC_{50}$ values to be expressed as nanomolar (NE) or millimolar (KCL) concentrations.

lipopolysaccharide, 10 ng/ml.

§$P < 0.05$ in comparison to untreated control.

[1]Number of rings in each treatment group.

The depressive actions of LPS were blocked by co-incubation of the tissue with the PKC inhibitor H7. $EC_{50}$ and $E_{max}$ values for rings treated with LPS and H7 were not significantly different from control tissue (Table I, FIG. 1A). Incubation of tissue with H7 by itself resulted in little change in contractile function (FIG. 1A.)

Incubation of rings with HA1004 which inhibits cAMP dependent, cGMP dependent, and myosin light chain kinases, but not PKC, to an extent comparable to H7 (20), was ineffective in blocking the effects of LPS on the tissue. Aortic rings incubated with LPS in the presence of HA1004 displayed significantly depressed sensitivity (Table I) and maximum contraction (FIG. 1B) to NE in comparison to control tissue. Incubation of tissue with HA1004 by itself resulted in a significant decrease in sensitivity to NE (Table I) and an apparent, but non-significant, diminution in maximum contraction (FIG. 1B).

Figure 2:
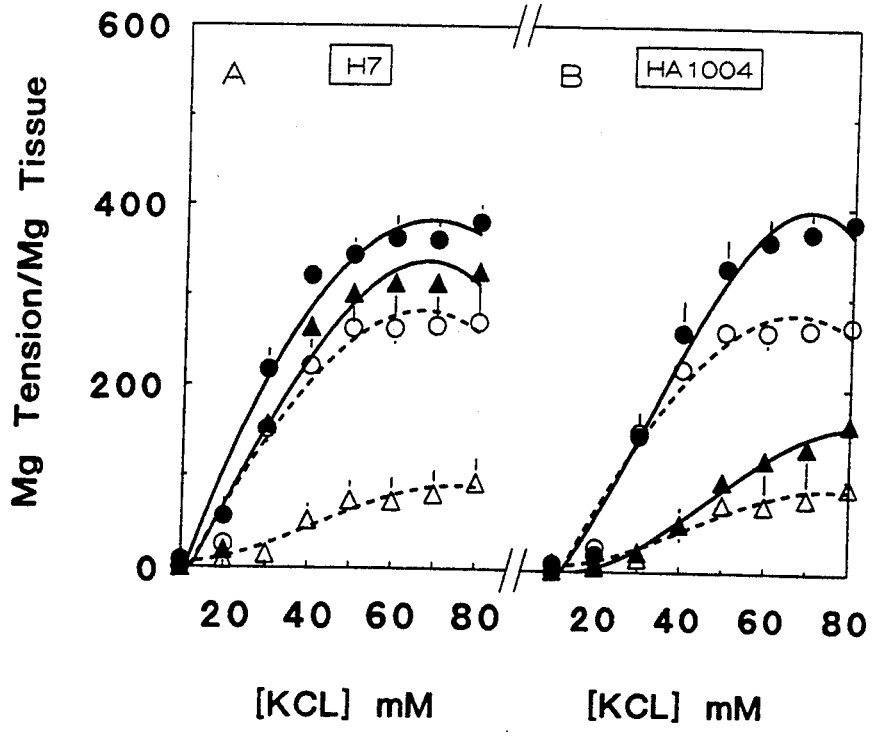
FIG. 2 is a graph showing contraction to cumulative doses of KCl by rat aortic rings incubated for 16 hr in combinations of control, LPS, H7, and HA1004 treated media. (Panel A) Response by rings incubated in medium only (open circles), medium plus H7 (25 μM, closed circles), medium containing LPS (10 ng/ml, open triangles), and medium containing LPS plus H7 (closed triangles). (Panel B) For clarity in presentation, responses by rings incubated in medium only (open circles) and LPS treated medium (open triangles) are reproduced from Panel A. Additional rings were incubated in medium plus HA1004 (25 μM, closed circles), and medium containing LPS plus HA1004 (closed triangles). Rings were prepared and data is presented as described in FIG. 1. N=6 rats.

Aortic rings incubated with LPS exhibited significantly diminished sensitivity and maximum contraction to KCl (Table I, FIG. 2). Inhibition of PKC by H7 shielded the tissue from LPS-induced contractile dysfunction so that $EC_{50}$ and $E_{max}$ values for rings treated with both LPS and H7 did not vary significantly from control tissue (Table I, FIG. 2A). Incubation with HA1004 did not protect the tissue against LPS-induced diminished sensitivity to KCl (Table I); however, treatment with HA1004 did result in a small but significant protection of maximal contractile performance (FIG. 2B). Treatment of control rings with either H7 or HA1004 resulted in significant increases in maximum contraction (FIG. 2) with no enhancement in sensitivity to KCl (Table I).

EXAMPLE 4

Figure 3:
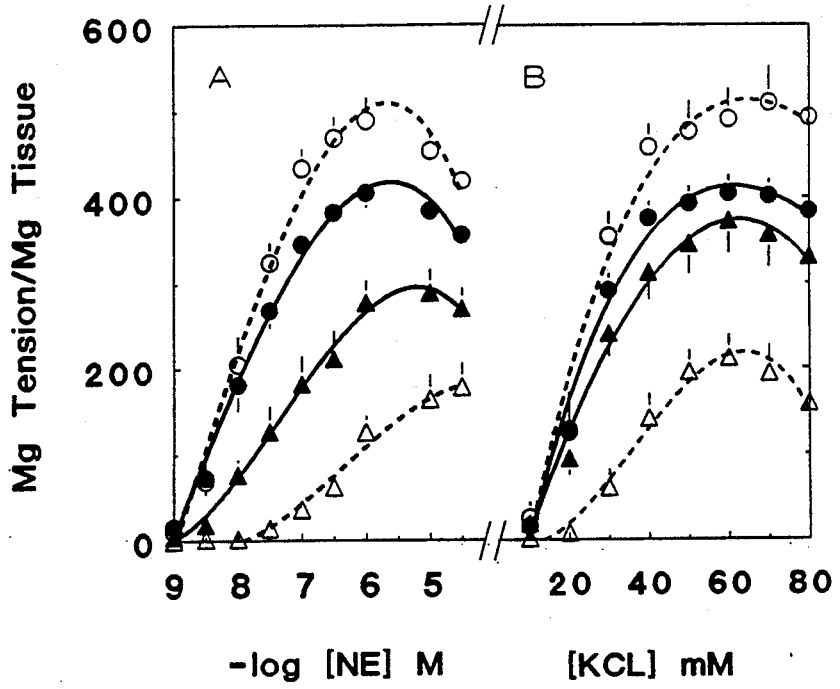
FIG. 3 is a graph showing contraction to cumulative doses of NE and KCl by rat de-endothelialized aortic rings incubated for 16 hr in combinations of control, LPS, and sphingosine treated media. (Panel A) Contraction to NE by rings incubated in medium only (open circles), medium plus sphingosine (20 μM, closed circles), medium containing LPS (35 ng/ml, open triangles), and medium containing LPS plus sphinogosine (closed triangles). (Panel B) Contraction to KCl by rings incubated and denoted with the same symbols as detailed above. Four rings were prepared from each rat and one ring allocated into each medium formulation to evaluate responses to NE. Rings were similarly prepared to determine responses to KCl. Data is presented as in FIG. 1. N=7 rats apiece for assessment of responses to NE and KCl.

The amelioration of LPS-induced vascular contractile dysfunction by inhibition of PKC was further explored in de-endothelialized aortic rings incubated with D-sphingosine. The de-endothelialized rings were incubated with 35 ng/ml LPS instead of 10 ng/ml because such rings are not as sensitive to LPS as tissue with an intact endothelium (14). The effective removal of the endothelium was confirmed by the lack of relaxation to acetylcholine by pre-contracted rings during the conditioning procedure. Rings incubated only with sphingosine exhibited suppressed contractions to NE and KCl (FIG. 3); it is possible that this suppression was due to the continued presence of the PKC inhibitor in the tissue during measures of contraction. Despite the suppression due to sphingosine itself, rings exposed to sphingosine were significantly protected against the suppressive impact of LPS on NE and KCl-induced contractions (FIG. 3). Rings treated with a combination of LPS and sphingosine were more sensitive to NE than rings exposed only to LPS ($P<0.05$), although the sensitivity of the rings exposed to the combined treatments remained less than that of control rings (Table I). Sphingosine treated rings exhibited $EC_{50}$'s for KCl that were not significantly different from control rings whether or not LPS was present, whereas rings treated only with LPS displayed significant losses in sensitivity to KCl (Table I).

EXAMPLE 5

Figure 4:
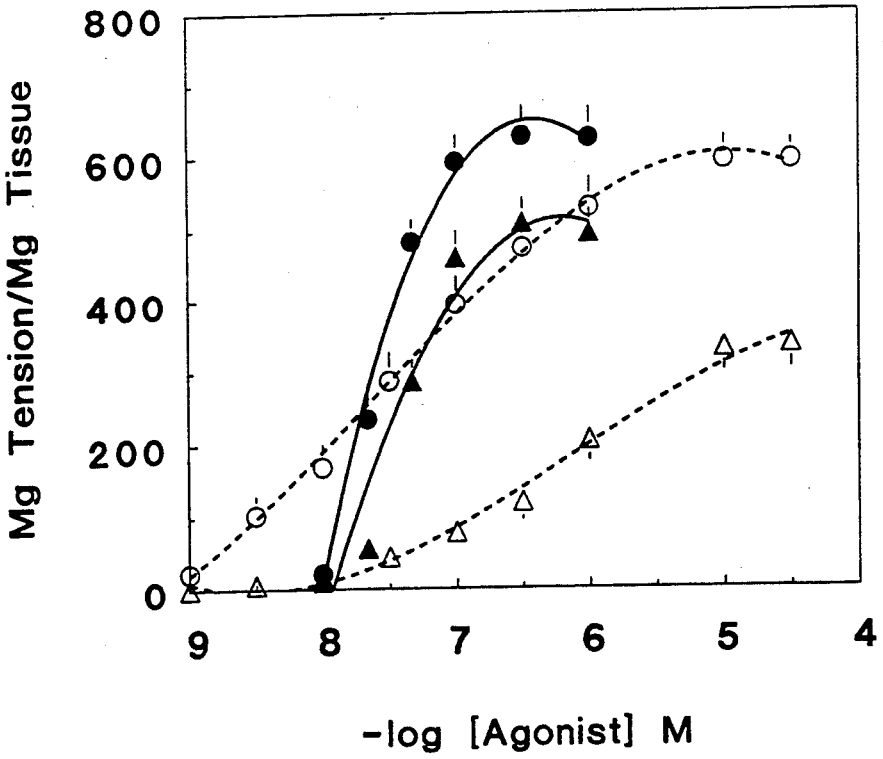
FIG. 4 is a graph showing contraction to cumulative doses of NE and 4β-phorbol-12,13-dibutyrate (PDB, a phorbol ester activator of PKC) by rat aortic rings incubated for 16 hr in control and LPS treated media. Rings incubated in medium only (open circles), and medium containing LPS (10 ng/ml, open triangles) were contracted with NE. Rings incubated in medium only (closed circles), and LPS treated medium (closed triangles) were contracted with PDB. Four rings were prepared from each rat and one ring allocated into each medium formulation. Data is presented as in FIG. 1. N=10 rats.

Influence of PDB on aortic contractile performance. Rings incubated with LPS and then contracted with PDB performed much better than identically incubated sister rings contracted with NE (FIG. 4). Nevertheless, these rings displayed a small but significant loss in maximum contractile performance compared to control incubated rings (FIG. 4); their sensitivity to PDB was also impaired by exposure to LPS (41±3 nM vs control $EC_{50}$ of 32±4 nM, $P<0.05$).

Aortic rings were significantly impaired in maximal contraction and sensitivity to NE after incubation with 1 or 10 μM PDB for 18 hr (FIG. 5A, Table II).

TABLE II $EC_{50}$ Values for Rat Aortic Rings after Incubation with 4β and 4α-Phorbor Dibutyrate for 16 h.

| Treatment | NE (nM)* | KCl (mM)* |
|---|---|---|
| Rings incubated with 4β-PDB | | |
| None | 75 ± 18 | 24 ± 2 |
| 4β-PDB (0.1 μM) | 56 ± 12 | 22 ± 1 |
| 4β-PDB (1.0 μM) | 184 ± 43§ | 27 ± 3 |
| 4β-PDB (10.0 μM) | 283 ± 136§ | 36 ± 2§ |
| N[1] | (6) | (6) |
| Rings incubated with 4α-PDB | | |
| None | 193 ± 69 | 33 ± 2 |
| 4α-PDB (10.0 μM) | 286 ± 128 | 28 ± 1 |
| N | (8) | (8) |

*$EC_{50}$ values calculated as described in Table I.
§$P < 0.05$ in comparison to untreated control.
[1]Number of rings in each treatment group.

Figure 5:
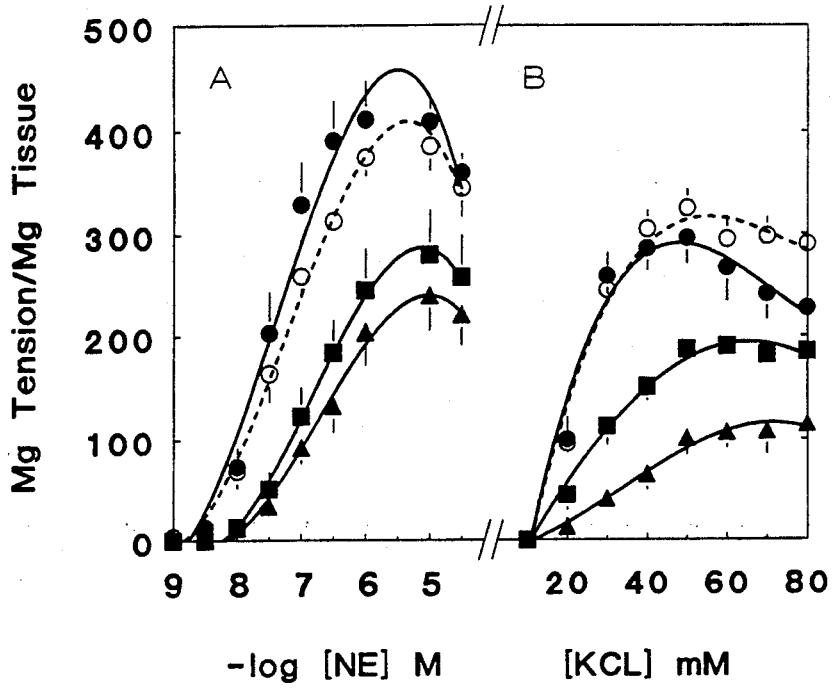
FIG. 5 is a graph showing contraction to cumulative doses of NE and KCl by rat aortic rings incubated for 16 hr in control and PDB treated media. (Panel A) Contraction to NE by rings incubated in medium only (open circles), or medium containing 0.1 μM (closed circles), 1.0 μM (closed squares), and 10 μM (closed triangles) PDB. (Panel B) Contraction to KCl by rings incubated and denoted with the same symbols as detailed above. Four rings were prepared from each rat and one ring allocated into each medium formulation to evaluate responses to NE. Rings were similarly prepared to determine responses to KCl. Data presented as in FIG. 1. N=6 rats apiece for assessment of responses to NE and KCl.
Figure 6:
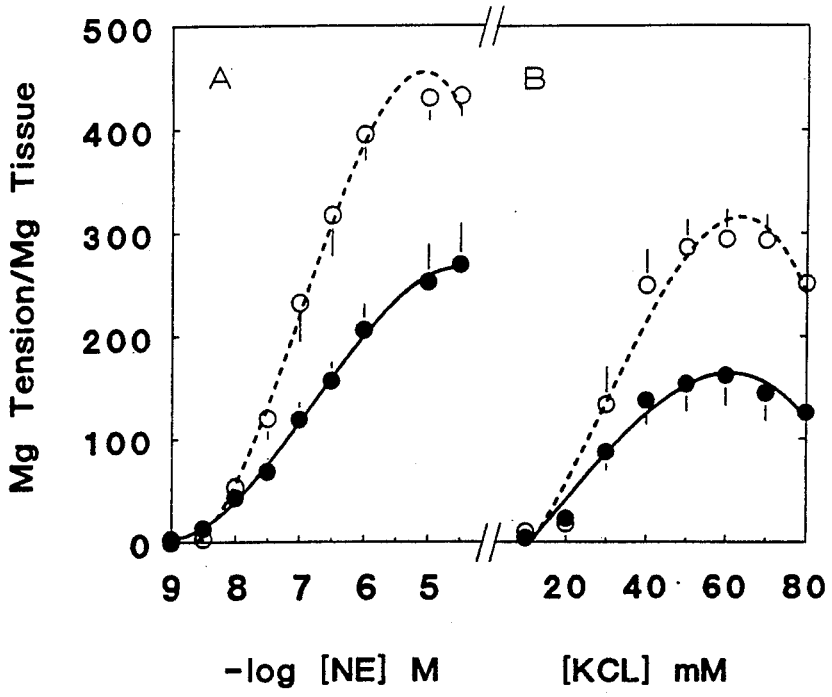
FIG. 6 is a graph showing contraction to cumulative doses of NE and KCl by rat aortic rings incubated for 16 hr in control and 4-α-phorbol-12,13-dibutyrate (4α-PDB, an inactive isomer of PDB used as a negative control for PDB) treated media. (Panel A) Contraction to NE by rings incubated in medium only (open circles), or medium containing 10 μM (closed circles) PDB. (Panel B) Contraction to KCl by rings incubated and denoted with the same symbols as detailed above. Four rings were prepared from each rat and one ring allocated into each medium formulation. Data is presented as in FIG. 1. N=8 rats for assessment of responses to both NE and KCl.

Other rings incubated with 1 or 10 μM PDB also showed significantly diminished contractions when stimulated with KCl (FIG. 5B); these rings were also less sensitive to KCl after exposure to 10 μM PDB (Table II). However, long-term incubation of rings with 0.1 μM PDB was ineffective in altering maximum contraction or sensitivity to NE or KCl (FIG. 5, Table II). Because 0.1 μM PDB is capable of causing greater than 90% of maximum contraction when applied to control tissue (FIG. 4), the possibility that the diminished contractile function that occurred after incubation with high concentrations of PDB was due to non-specific effects was tested by incubation with 10 μM 4α-PDB, which is an inactive isomer of PDB. Rings incubated with this isomer also displayed significantly impaired contractions to NE and KCl (FIG. 6) with no significant alterations in $EC_{50}$ values for the agonists (Table II).

EXAMPLE 6

Figure 7:
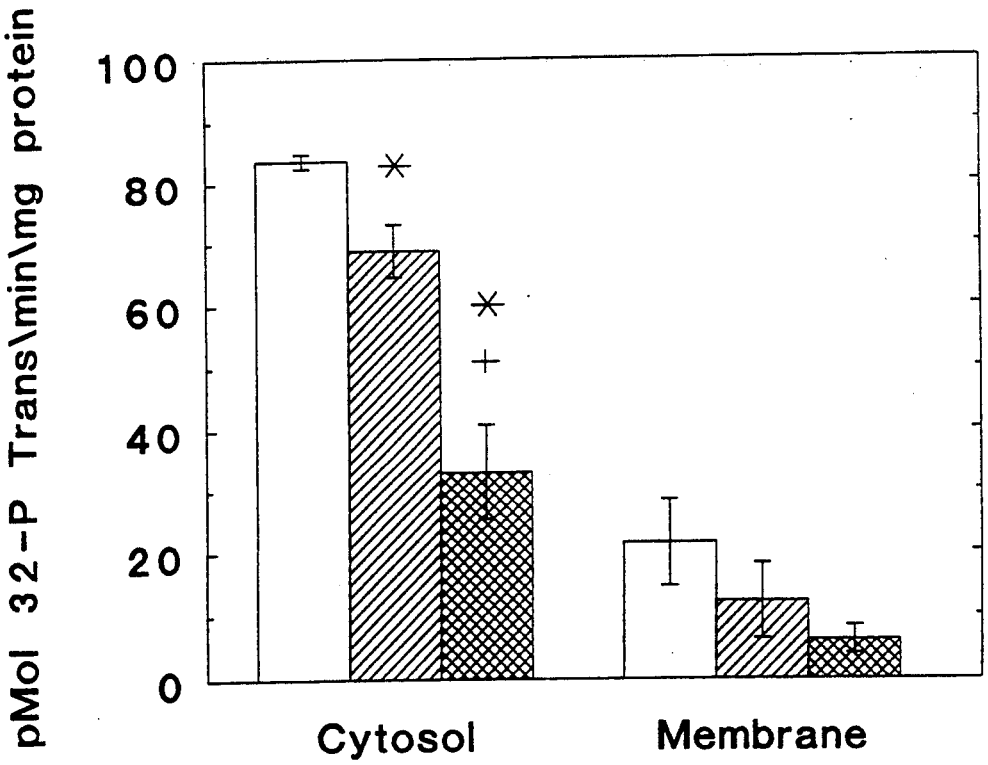
FIG. 7 is a graph showing protein kinase C activity in rat aortic rings incubated for 16 hr in control, LPS, and PDB treated media. PKC activity was measured in rings incubated in medium only (open histograms), medium with 10 ng/ml LPS (striated), and medium with 1.0 μM PDB (crosshatched). (*) denotes significant decreases in cytosolic PKC activity in LPS and PKC-incubated rings in comparison to control rings; (+) indicates significantly less cytosolic PKC activity in PDB-incubated rings in comparison to LPS-incubated rings. The data are plotted as means±SEM. N=12 rats (4 rats per treatment group).

Influence of LPS and PDB on vascular cell PKC activity. No differences in PKC activity were apparent between endothelium-intact and de-endothelialized rings (data not shown); therefore data from both preparations were pooled to assess the effects of LPS and PDB on PKC activity. Long-term incubation of vascular tissue with 1.0 μM PDB resulted in large decreases in PKC activity in the cytosolic fraction and nonsignificant decreases in the membrane fraction (FIG. 7). Incubation of vascular tissue with 10 ng/ml LPS produced similar results, although the magnitude of decrease in PKC activity was less (FIG. 7).

DISCUSSION

PKC activity is embodied in at least seven related proteins that have distinct tissue distributions and enzymatic properties (see 21 for review). The presence of multiple, functionally distinct PKC subtypes in tissues is likely to confer complex cellular responses to PKC activators and inhibitors. In general, PKC is characterized as a $Ca^{2+}$ and phospholipid dependent enzyme that is activated synergistically by elevated intracellular $Ca^{2+}$ and diacylglycerol (DAG) resulting from receptor initiated hydrolysis of phosphatidylinositol-4,5-bisphosphate ($PIP_2$). Phorbol esters such as PDB can directly substitute for DAG in the activation of PKC and therefore bypass the requirement for receptor stimulation to mobilize this enzyme. However, some PKC subtypes (isozymes) can be activated by free fatty acids such as arachidonic acid in the absence of phospholipid and DAG (22). Three separate PKC subtypes have been shown to express distinctly different dependencies on $Ca^{2+}$ when activated by PDB (23). In addition, a single PKC subtype from bovine brain exhibited requirements for phospholipid, DAG, and $Ca^{2+}$ that varied according to the substrate presented to the kinase (24). Conversely, the inhibitory efficacy of PKC inhibitors depends upon the stimulus that activates the kinase. Schachtele et al (25) demonstrated that aggregation of platelets after stimulation with thrombin, 1-oleyl-2-acetylrac-glycerol (OAG), linoleic or linolelaidic acid was blocked by pretreatment with the PKC inhibitors polymyxin B, H-7, and staurosporine. The inhibitors showed distinct patterns of potency in blocking aggregation that depended on the aggregation-inducing stimulus; an inhibitor that was relatively ineffective at blocking aggregation to one stimulus was much more effective at countering aggregation to a different stimulus, while the other inhibitors manifested reverse patterns of anti-aggregatory potency.

The complex relationship between activators and inhibitors of PKC is apparent in vascular tissue. H7 is an ineffective blocker of PDB induced contraction in deendothelialized rat aortas, but significantly inhibits KCl elicited contraction (26). Excess $K^+$ activates PKC in sympathetic neurons (27) and data from rabbit femoral and renal arteries suggest that a similar relationship exists in vascular smooth muscle (28). Rabbit aortic smooth muscle cells express a PKC isozyme through which exposure to TPA modulates cell proliferation; the actions of this isozyme can be blocked by down regulating the kinase by long-term exposure of the cells to PDB before exposure to TPA. In the same cells, TPA also inhibits whole blood serum induced intracellular $Ca^{2+}$ mobilization; this inhibition of $Ca^{2+}$ mobilization occurs via a different PKC isozyme that cannot be down regulated by prior treatment with PDB (29).

In the present study, inhibition of PKC activity by inhibitors directed to either the active site (H7, 20) or the regulatory site (sphingosine, 19) of the enzyme clearly abrogated the majority of the deleterious effects of LPS on rat aortic tissue contractile function. The protection accruing from PKC blockade was present whether contraction was stimulated via receptor or non-receptor mechanisms and implicates a role for PKC in transducing LPS stimulated vascular contractile dysfunction. The data further suggest that the majority of the lesion in contractile function occurs at a more fundamental level than the $\alpha_1$-receptor, because KCl induced contractions (non-receptor mediated) are sensitive to inhibition by LPS and protection by the PKC inhibitors. Some $\alpha_1$-receptor associated impairment may be present, however, because tissue exposed to LPS and H7 or sphingosine uniformly showed less maintenance of control level responses when stimulated with NE (FIGS. 1A and 3A) than did similarly incubated tissue stimulated with KCl (FIGS. 2A and 3B).

The aortic ring model used to derive these observations embodied conflicting experimental requirements. It was necessary to first block PKC activity during incubation, and then wash the inhibitors from the tissue to allow PKC action to support contraction. At the same time, it was unknown whether LPS can be washed from the tissue after a long-term exposure, or whether LPS induced vascular dysfunction would increase as PKC activity recovered during the wash procedure. The wash time selected (90 min) was a compromise between these criteria; in this model, measures of the beneficial results of PKC inhibition during exposure to LPS probably reflect an underestimate of the importance of PKC activity to LPS induced vascular suppression. With regard to sphingosine, it is likely that a meaningful amount of the inhibitor remained in the rings during testing because rings incubated only with sphingosine manifested significantly diminished maximum contractions to NE and KCl (FIG. 2). The persistence of the inhibitor was not so great, however, that it masked the protection accorded by PKC inhibition during LPS exposure. It is likely that H7 and HA1004 were washed from the tissue before assessment of contraction because rings incubated only with these agents displayed normal or enhanced contractions to NE or KCl. While treatment of rings with HA1004 tended to suppress ring responses to NE (FIG. 1B, Table I), similarly incubated and washed rings expressed augmented contractile responses to KCl (FIG. 2B). These results suggest that HA1004 alters $\alpha_1$-receptor meditated contraction by an undefined mechanism that is not related to its continued presence in the tissue.

Long-term treatment of aortic rings with LPS provoked a small but significant decrease in tissue PKC activity (FIG. 7) suggesting that LPS either directly or via intracellular second messenger causes a meaningful activation of the enzyme. The proportional decreases in PKC activity in the cytosolic and membrane fractions of rat aortic rings after an 18 hr exposure to LPS or PDB are similar to those described by Stassen et al (30) for cultured rat aorta derived cells exposed to PDB for 24 hr.

In contrast to the above observations, incubation of tissue with PDB at a concentration that elicits almost maximal contraction (0.1 $\mu$M, FIG. 4) did not induce contractile defects. The suppression observed after exposure to larger concentrations of PDB probably reflects non-specific effects of phorbols on the tissue, because the inactive isomer 4$\alpha$-PDB is equally effective at causing vascular suppression. 4$\alpha$-PDB itself could not contract aortic rings at concentrations up to 10 $\mu$M (data not shown). There are several possibilities why PDB cannot impart an LPS-like suppression of vascular tissue during prolonged incubation: 1) PDB does not stimulate an appropriate isotype of PKC to carry the signal for vascular suppression, 2) PDB down regulates PKC activity to such a large extent (FIG. 7) that it actually blocks the transduction of the suppressive signal, and 3) PKC activation is necessary but not sufficient to cause an LPS-like vascular suppression. Support for the last alternative comes from a report that PKC activity is required for the synthesis of platelet activating factor and leukotriene $B_4$ in A23187 stimulated human neutrophils; however, stimulation of the neutrophils with PMA alone could not cause synthesis of either PAF or $LTB_4$ (31).

The events that occur proximate and distal to PKC activation are unclear. Evidence for second messenger coupled receptors for LPS in mammalian cells is very sparse (see 32 for review) and none have been described in vascular smooth muscle. An alternate method for introducing LPS to intracellular mechanisms may exist in which cell surface molecules bind LPS and facilitate a subsequent insertion of the LPS into the cell membrane (32). The lipid A moiety of LPS can directly activate PKC in vitro (33,34). The sequence of events that follow PKC activation and ultimately result in vascular suppression are poorly understood. We have shown that induction of vascular contractile dysfunction by LPS requires de novo protein synthesis (14). A good candidate for such a protein is nitric oxide synthase that is newly synthesized by rat aortic smooth muscle cells after exposure to LPS (35). Augmented levels of this $Ca^{2+}$ independent enzyme generate nitric oxide that in turn activates soluble guanylate cyclase to produce cGMP, resulting in suppression of vascular contractile function (36). LPS also stimulates rat aortas to enhance expression of mRNA for the proto-oncogene c-myc (37). Expression of this proto-oncogene is associated with initiation of vascular smooth muscle proliferation (38); we speculate that alterations in the phenotype of vascular smooth muscle cells are likely to be reflected by altered functional performance as well. LPS induced expression of c-myc in vascular smooth muscle cells has not been shown to be via PKC activation; however, this is a likely occurrence because another proto-oncogene that has proliferative actions, c-fos, is expressed after activation of PKC in rat aortic smooth muscle cells (39). Finally, it is not necessary to postulate a mechanism of vascular suppression that depends on the amplified synthesis of any protein. It is conceivable that LPS induced vascular suppression is mediated via a constitutively expressed protein that is no longer produced after inhibition of protein synthesis. PKC phosphorylates a large number of substrates that may modulate contractile function (see 40 for review); an accumulation of phosphates on individual molecular entities could enhance the activity of molecules that negatively regulate the contractile process.

Prolonged exposure of rat aortas to small concentrations of LPS results in impaired contractions to receptor and non-receptor mediated stimuli. The acquisition of contractile dysfunction can be prevented by inhibition of PKC by sphingosine and sphingosine analogues implicating PKC as an intracellular mediator of LPS action in vascular smooth muscle cells. In addition, cellular PKC activity is significantly reduced after prolonged exposure to LPS, suggesting that LPS executes a persistent stimulation of PKC. Because exposure of the tissue to PDB could not produce a defective contractile state, it is possible that PKC activation is necessary but not sufficient to transduce LPS effects on vascular tissue, although alternate explanations for the lack of impact of PDB on contractile function are possible. The fundamental requirement for PKC activation to mediate the vascular suppressive actions of LPS has significant implications for therapeutic intervention in sepsis or endotoxemia.

REFERENCES

1. Magnuson, D. K., R. V. Maier, and T. H. Pohlman. 1989. Protein kinase C: A potential pathway of endothelial cell activation by endotoxin, tumor necrosis factor, and interleukin-1. Surgery 106:216–223.
2. Lane, T. A., G. E. Lamkin, and E. V. Wancewicz. 1990. Protein kinase C inhibitors block the enhanced expression of intercellular adhesion molecule-1 on endothelial cells activated by interleukin-1, lipopolysaccharide and tumor necrosis factor. Biochem. Biophys. Res. Comm. 172:1273–1281.
3. Lynch, J. J., T. J. Ferro, F. A. Blumenstock, A. M. Brockenauer, and A. B. Malik. 1990. Increased endothelial albumin permeability mediated by protein kinase C activation. J. Clin. Invest. 85:1991–1998.
4. Jiang, M. J., and K. G. Morgan. 1987. Intracellular calcium levels in phorbol ester-induced contractions of vascular muscle. Am. J. Physiol. 253:H1365–H1371.
5. Nishimura, J., R. A. Khalil, J. P. Drenth, and C. van Breemen. 1990. Evidence for increased myofilament $Ca^{2+}$ sensitivity in norepinephrine-activated vascular smooth muscle. Am. J. Physiol. 259:H2–H8.
6. Chiu, A. T., J. M. Bozarth, M. S. Forsythe, and P. B. M. W. M. Timmermans. 1987. $Ca^{++}$ utilization in the construction of rat aorta to stimulation of protein kinase C by phorbol dibutyrate. J. Pharmacol. Exp. Ther. 242:934–939.
7. Khalil, R. A., and C. van Breemen. 1988. Sustained contraction of vascular smooth muscle: Calcium influx or C-kinase activation? J. Pharmacol. Exp. Ther. 244:537–542.
8. Furukawa, K. I., Y. Tawada, and M. Shigekawa. 1989. Protein kinase C activation stimulates plasma membrane $Ca^{2+}$ pump in cultured vascular smooth muscle cells. J. Biol. Chem. 264:4844–4849.
9. Galizzi, J. P., J. Qar, M. Fosset, C. van Renterghem, and M. Ladzdunski. 1987. Regulation of calcium channels in aortic muscle cells by protein kinase C activators (diacylglycerol and phorbol esters) and by peptides (vasopressin and bombesin) that stimulate phosphoinositide breakdown. J. Biol. Chem. 262:6947–6950.
10. Colucci, W. S., M. A. Gimbrone Jr., and R. W. Alexander. 1986. Phorbol diester modulates $\alpha$-adrenergic receptor-coupled calcium efflux and $\alpha$-adrenergic receptor number in cultured vascular smooth muscle cells. Circ. Res. 58:393–398.
11. Brock, T. A., S. E. Rittenhouse, C. W. Powers, L. S. Ekstein, M. A. Gimbrone, Jr., and R. W. Alexander. 1985. Phorbol ester and 1-oleoyl-2-acetylglycerol inhibit angiotensin activation of phospholipase C in cultured vascular smooth muscle cells. J. Biol. Chem. 260:14158–14162.
12. Aiyar, N., P. Nambi, M. Whitman, F. L. Stassen, and S. T. Crooke. 1987. Phorbol ester-mediated inhibition of vasopressin and $\beta$-adrenergic responses in a vascular smooth muscle cell line. Molecular Phormacol. 31:180–184.
13. McKenna, T. M., and W. A. W. Titius. 1989. Role of monokines in altering receptor and non-receptor mediated vascular contraction in sepsis. In Molecular and Cellular Mechanisms of Septic Shock, B. Roth, T. Nielsen, and A. McKee, editors. Alan R. Liss, Inc., New York. 279–303.
14. McKenna, T. M. 1990. Prolonged exposure of rat aorta to low levels of endotoxin in vitro results in impaired contractility. Association with vascular cytokine release. J. Clin. Invest. 86:160–168.
15. Thomas, T. P., R. Gopalakrishna, and W. B. Anderson. 1987. Hormone- and tumor promoter-induced activation or membrane association of protein kinase C in intact cells. In Methods in Enzymology. P. M. Conn, and A. R. Means, editors. Academic Press, Inc., Orlando, Fla. 141:399–411.
16. Nelson, D. P., and L. D. Homer. 1983. Non-linear regression analysis: a general program for data modeling using personal microcomputers. Report No. 83-5. Naval Health Research Center, San Diego, Calif. 20 pp.
17. Fleming, W. W., D. P. Westfall, I. S. De La Lande, and L. B. Jellett. 1972. Log-normal distribution of equieffective doses of norepinephrine and acetylcholine in several tissues. J. Pharmacol. Exp. Ther. 181:339–345.
18. Sokal, R. R., and F. J. Rohlf. 1969. Biometry. W. H. Freeman and Co., San Francisco, Calif. 776 pp.
19. Merrill Jr., A. H., S. Nimkar, D. Menaldino, Y. A. Hannun, C. Loomis, R. M. Bell, S. R. Tyagi, J. D. Lambeth, V. L. Stevens, R. Hunter, and D. C. Liotta. 1989. Structural requirements for long-chain (sphingoid) base inhibition of protein kinase C in vitro and for the cellular effects of these compounds. Biochemistry 28:3138–3145.
20. Hidaka, H., M. Inagaki, S. Kawamoto, and Y. Sasaki. 1984. Isoquinolinesulfonamides, novel and potent inhibitors of cyclic nucleotide dependent protein kinase and protein kinase C. Biochemistry 23:5036–5041.
21. Nishizuka, Y. 1988. The molecular heterogeneity of protein kinase C and its implications for cellular regulation. Nature 334:661–665.
22. Sekiguchi, K., M. Tsukuda, K. Ogita, U. Kikkawa, and Y. Nishizuka. 1987. Three distinct forms of rat brain protein kinase C: differential response to unsaturated fatty acids. Biochem. Biophys. Res. Comm. 145:797–802.
23. Jaken, S., and S. C. Kiley. 1987. Purification and characterization of three types of protein kinase C from rabbit brain cytosol. Proc. Natl. Acad. Sci. USA. 84:4418–4422.
24. Bazzi, M. D., and G. L. Nelsestuen. 1987. Role of substrate in imparting calcium and phospholipid requirements to protein kinase C activation. Biochemistry 26:1974–1982.
25. Schachtele, C., R. Seifert, and H. Osswald. 1988. Stimulus-dependent inhibition of platelet aggregation by the protein kinase C inhibitors polymyxin B, H-7 and staurosporine. Biochem. Biophys. Res. Comm. 151:542–547.
26. Auguet, M., S. Delaflotte, P. E. Chabrier, and P. Braquet. 1989. Comparative effects of endothelin and phorbol 12-13 dibutyrate in rat aorta. Life Sci. 45:2051–2059.
27. Wakade, A. R., T. D. Wakade, R. K. Malhotra, and S. V. Bhave. 1988. Excess $K^+$ and phorbol ester activate protein kinase C and support the survival of chick sympathetic neurons in culture. J. Neurochem. 51:975–983.

28. Ratz, P. H. 1990. Effect of the kinase inhibitor, H-7, on stress, crossbridge phosphorylation, muscle shortening and inositol phosphate production in rabbit arteries. J. Pharmacol. Exp. Ther. 252:253–259.

29. Kariya, K. I., Y. Kawahara, H. Fukuzaki, M. Hagiwara, H. Hidaka, Y. Fukumota, and Y. Takai. 1989. Two types of protein kinase C with different functions in cultured rabbit aortic smooth muscle cells. Biochem. Biophys. Res. Comm. 161:1020–1027.

30. Stassen, F. L., D. B. Schmidt, M. Papadopoulos, and H. M. Sarau. 1989. Prolonged incubation with phorbol esters enhanced vasopressin-induced calcium mobilization and polyphosphatidylinositol hydrolysis of vascular smooth muscle cells. J. Biol. Chem. 264:4916–4923.

31. McIntyre, T. M., S. L. Reinhold, S. M. Prescott, and G. A. Zimmerman. 1987. Protein kinase C activity appears to be required for the synthesis of platelet-activating factor and leukotriene $B_4$ by human neutrophils. J. Biol. Chem. 262:15370–15376.

32. Morrison, D. C. 1989. The case for specific lipopolysaccharide receptors expressed on mammalian cells. Microbial Pathogenesis 7:389–398.

33. Wightman, P. D., and C. R. H. Raetz. 1984. The activation of protein kinase C by biologically active lipid moieties of lipopolysaccharide. J. Biol. Chem. 259:10048–10052.

34. Romano, M., and J. Hawigers. 1990. Interaction of endotoxic lipid A and lipid X with purified human platelet protein kinase C. J. Biol. Chem. 265:1765–1770.

35. Rees, D. D., S. Cellek, R. M. J. Palmer, and S. Moncada. 1990. Dexamethasone prevents the induction by endotoxin of a nitric oxide synthase and the associated effects on vascular tone: an insight into endotoxin shock. Biochem. Biophys. Res. Comm. 173:541–547.

36. Knowles, R. G., M. Salter, S. L. Brooks and S. Moncada. 1990. Anti-inflammatory glucocorticoids inhibit the induction endotoxin of nitric oxide synthase in the lung, liver, and aorta of the rate. Biochem. Biophys. Res. Comm. 172:1042–1048.

37. Carcillo, J. A., and C. J. Hough. 1989. Oncogene expression: a new horizon in the study of sepsis. In Molecular and Cellular Mechanisms of Septic Shock. B. Roth, T. Nielsen, and A. McKee, editors. Alan R. Liss, Inc., New York. 71–76.

38. Miano, J. M., R. R. Tota, N. Vlasc, K. J. Danishefsky, and M. B. Stemerman. 1990. Early protooncogene expression in rat aortic smooth muscle cells following endothelial removal. Am. J. Pathol. 137:761–765.

39. Kawahara, Y., M. Sunako, T. Tsuda, H. Fukuzaki, Y. Fukumoto, and Y. Takai. 1988. Angiotensin II induces expression of the c-fos gene through protein kinase C activation and calcium ion mobilization in cultured vascular smooth muscle cells. Biochem. Biophys. Res. Comm. 150:52–59.

40. Rasmussen, H., Y. Takuwa, and S. Park. 1987. Protein kinase C in the regulation of smooth muscle contraction. FASEB J. 1:177–185.

41. Igarashi, Y., Hakamori, S-I, Toyokuni, T., Dean, B., Shushi, F., Sugimoto, M., Ogawa, T., El-Ghendy, K., and E. Racker. 1989. Effect of chemically well-defined sphingosine and its N-methyl derivatives on protein kinase C and src kinase activities. Biochemistry 28:6796–6800.

42. Hannun, Y. A. and R. M. Bell. 1989. Functions of sphingolipids and sphingolipid breakdown products in cellular regulation. Science 243:500–507.

Obviously, many modifications and variations of the present invention are possible in light of the above teachings. It is therefore to be understood that, within the scope of the appended claims, the invention may be practiced otherwise than as specifically described.

What we claimed is:

1. A therapy for septic shock which reduces inflammation and improves tissue and organ perfusion comprising infusing between about 0.1 to 50 mg/kg body weight of a PKC inhibitor selected from the group consisting of lipid analoges in a pharmaceutically acceptable carrier into a entity at risk of septic shock.

2. The therapy of claim 1 wherein the lipid analogue is a sphingosine analogue selected from the group consisting of 4-trans-sphingenine (sphingosine), dihydrosphingosine (sphinganine), 4-D-hydroxysphinganine (phytosphingosine) and homologs.

3. The therapy of claim 2 wherein the lipid analogue is sphingosine.

4. The therapy of claim 2 containing about 0.5 to 25 mg/Kg body weight of the lipid analog.

5. The therapy of claim 4 containing about 1.0 to 5.0 mg/Kg body weight of the lipid analog.

6. The therapy of claim 3 containing about 0.5 to 25 mg/Kg body weight of the lipid analog.

7. The therapy of claim 6 containing about 1.0 to 5.0 mg/Kg body weight of sphingosine.

8. The therapy of claim 3 wherein the carrier is formed by dissolving the lipid sequentially in ethanol, polyoxyethylene sorbitan mono-oleate (Tween 80), and polyethylene glycol 300 molecular weight (PEG 300) followed by mixing the dissolved lipid with albumin.

* * * * *